(12) United States Patent
Pan et al.

(10) Patent No.: US 8,703,456 B2
(45) Date of Patent: Apr. 22, 2014

(54) METHOD FOR MANUFACTURING RED MOLD DIOSCOREA

(71) Applicant: SunWay Biotech Co., Ltd., Taipei (TW)

(72) Inventors: Tzu-Ming Pan, Taipei (TW); Chun-Lin Lee, Taipei (TW)

(73) Assignee: Sunway Biotech Co., Ltd. (TW)

( * ) Notice: Subject to any disclaimer, the term of this patent is extended or adjusted under 35 U.S.C. 154(b) by 0 days.

(21) Appl. No.: 13/950,369

(22) Filed: Jul. 25, 2013

(65) Prior Publication Data

US 2013/0309731 A1 Nov. 21, 2013

Related U.S. Application Data

(60) Division of application No. 13/465,029, filed on May 7, 2012, which is a continuation-in-part of application No. 12/690,379, filed on Jan. 20, 2010, now abandoned.

(30) Foreign Application Priority Data

Apr. 24, 2009 (TW) .............................. 98113815 A

(51) Int. Cl.
 *C12P 1/02* (2006.01)
 *C12P 17/00* (2006.01)
(52) U.S. Cl.
 USPC ........... 435/171; 435/117; 435/118; 435/119; 435/911
(58) Field of Classification Search
 None
 See application file for complete search history.

(56) References Cited

U.S. PATENT DOCUMENTS

| 4,145,254 | A | * | 3/1979 | Shepherd et al. ............. 435/132 |
| 4,447,530 | A | | 5/1984 | Young |
| 5,534,280 | A | * | 7/1996 | Welch ........................... 426/321 |
| 6,635,467 | B2 | | 10/2003 | Chen et al. |

FOREIGN PATENT DOCUMENTS

| JP | 363198973 | * | 8/1988 |
| JP | 2000060536 | * | 2/2000 |

OTHER PUBLICATIONS

Pisareva et al. "Taxonomic investigation and growth characteristics of citrinin free *Monascus pilosus* C1 strain". Biotechnol. & Biotechnol. Eq. 2006, pp. 88-96.*
Chun-Lin Lee et al. "*Monascus* fermentation of dioscorea for increasing the production of cholesterol-lowering agent—monacolin K and antiinflammation agent—monascin". Appl. Microbiol Biotechnol (2006) 72:1254-1262.
Chun-Lin Lee et al. "Improving the ratio of monacolin K to citrin production or *Monascus purpureus* NTU 568 under dioscorea medium through the mediation of pH and ethanol addition". J agric Food Chen. Aug. 2007, vol. 55, No. 16, pp. 6493-6502.

* cited by examiner

*Primary Examiner* — Vera Afremova

(57) ABSTRACT

The present invention discloses a method for manufacturing red mold dioscorea, and the method comprises the following steps: washing and cutting a fresh dioscorea into pieces with a specific dimension; drying the pieces of the fresh dioscorea for making the dried dioscorea contain a specific water content and a specific sulfur content; adding some water with an appropriate ratio to fresh dioscorea or dried dioscorea; sterilizing the dioscorea; after the dioscorea being cooled down, inoculating the dioscorea with *Monascus* species; cultivating the dioscorea with an appropriate temperature, an appropriate humidity and an appropriate shacking frequency for an appropriate time period; and drying the cultivated red mold dioscorea with an appropriate water content.

4 Claims, 6 Drawing Sheets

METHOD FOR MANUFACTURING RED MOLD DIOSCOREA

BACKGROUND OF THE INVENTION

1. Field of the Invention

The present invention relates to a method for manufacturing red mold dioscorea, and more particularly relates to a method for manufacturing red mold dioscorea with a solid state cultivation method or a liquid state cultivation method.

2. Description of the Prior Art

Hypertension caused by hypercholesterol is a popular civilization disease in recent years. Following the advancement of medical science, populations of middle-aged and geriatric people are increasing. It is difficult to eliminate superoxide free radicals in middle-aged and geriatric people result from the lower metabolic mechanism, and the middle-aged and geriatric diseases include cancer and cardiopathy are prone to occur. Cardiovascular diseases arise from hypercholesterolemia include apoplexy, coronary atherosclerotic cardiopathy and hypertension. In pursue of the healthy diet in life, health food nowadays is very popular. Red mold products possess both effects of inhibition of cholesterol synthesis and blood pressure lowering and become one of the popular health food.

Numerous researches in recent years prove that red mold rice have significant lipid-lowering effect on hyperlipidemia hamsters, thus red mold rice have potential to be an ingredient in cholesterol-lowering drugs and improve this kind of disease. The above effects are result from that red mold rice can produce several kinds of secondary metabolite, such as cholesterol-synthesis inhibitor, blood pressure lowering material, anti-cancer material and so forth. Some previous researches about secondary metabolite of red mold yeast indicate that the yield and pattern of secondary metabolite may be directly or indirectly influenced by cultural environment and method.

Recently, red mold related products made by using some specific fermented substrate are proposed. In 2006, Lee et al. propose their study of "*Monascus* fermentation of dioscorea for increasing the product of cholesterol-lowing agent", and the study is then published on Journal of *Applied Microbial and Cell Physiology*. In Lee's study, *Monascus*-fermented substrate, for example, *Monascus* fermented dioscorea, is proven its effect on increasing the production of monaclin K and monascin, wherein the monaclin K can be used as a cholesterol-lowering agent and the monascin can be as a anti-inflammation agent.

Please refer to FIG. 1, there is shown a flowchart of a red mold substrate preparation method proposed by Lee. As shown in FIG. 1, to prepare the red mold substrate, a substrate is firstly purchased from local supermarket (S01'). Then, five grams of substrate is soaked in distilled water for 8 hr (S02'), and excess water is removed by using a sieve (S03'). After the steps of S01'~S03' are finished, the substrate is then autoclaved in a wood dish at 120° C. for 20 min (S04'). And after being cooled, the substrate is inoculated with a 5% spore suspension ($10^7$ spores/ml) and 0.3% ethanol (S05'). Therefore, the inoculated substrate is cultivated at 30° C. for 10 days (S06'); moreover, during the culturing stage, 145 ml of water is added once every 12 hr at a total of three times and the addition of water starts on the fifth day of cultivation. Therefore, Lee successfully stimulates the formation of monacolin K by adopting above-mentioned preparation method. In addition, Lee also finds that the *monascus*-fermented dioscorea have more amount of yellow pigment than *monascus*-fermented rice. Yellow pigment of *Monascus* species including monascin and ankaflavin has been shown as an anticancer agent and anti-inflammation agent.

Therefore, because Lee's preparation method is proven the effect on increasing the production of monaclin K and monascin, the preparation method is then widely used for the production of monaclin K and monascin, and called solid state cultivation method. However, in spite of Lee's preparation method is helpful to the production of monaclin K and monascin, his preparation method still includes the shortcomings and drawbacks as follows:

1. In the steps S02' and S03' of Lee's preparation method, the substrate is soaked in distilled water for 8 hr and the excess water is removed by using a sieve. The person skilled in this art is able to find that Lee still fails to optimize a best water ratio for soaking the substrate, and the water ration of steps S02' and S03' is obviously unsuitable to the sterilization of the substrate.

2. In Lee's preparation method, it does not provide a suitable environment for culturing the inoculated substrate, for example, a suitable environment with an optimal relative humidity. Water supplementation is used in Lee's preparation method, but the environment humanity control is more useful to stabilize the production of monacolin K, monascin, ankaflavin, and citrinin, the person skilled in this art knows that.

3. Although Lee's preparation method is proven the effect on increasing the production of monaclin K and monascin can be increased, it also helpful to increase the production of citrinin, which is grouped into a kind of polyketide derivatives of *Monascus*. So that Lee adds 0.3% (v/w) ethanol to substrate (dioscorea) in order to lower citrinin production. However, the procedure also significantly decreased the production of the formational metabolites monascin and ankaflavin by 2.5 and 3-fold.

In addition, differing from the solid state cultivation method for increasing the production of monaclin K and monascin, in 2007, Lee further proposes his study of "Improving the ratio of Monacolin K to citrinin production of *Monascus purpureus* NTU 568 under dioscorea medium through the mediation of pH value and ethanol addition", and the study is then published on Journal of *Agricultural and Food Chemistry*. In this study, Lee proposes a liquid state cultivation method for increasing the production of monaclin K and monascin. Please refer to FIG. 2, which illustrates a flowchart of the liquid state cultivation method proposed by Lee. As shown in FIG. 2, to prepare and culture the *monascus*-fermented dioscorea (substrate), a dry dioscorea root is firstly milled into powder (60-80 mesh) and used as the substrate of seed culture (S01"), and a culture medium with 5% the powdered dioscorea is then prepared (S02"). After the steps of S02'~S02' are finished, the culture medium is subsequently inoculated with 5% *Monascus* spore solution and 0.3% ethanol (S03"). Therefore, in step S04", the fermentation is carried out with aeration rate at 4 vvm, 30° C. and the agitation at 200 rpm for 12 days (S04"). After fermentation, the dioscorea is collected and dried at 55° C. for 48 hr (505"), and eventually to weight the total dry biomass for the calculation of the ratio of dry biomass weight to dioscorea added weight (B/D ratio) (S06").

Through the liquid state cultivation method, Lee successfully stimulates the formation of monacolin K and monascin. Besides, Lee also determines an optimum culture conditions based on experiment results. However, in spite of Lee's liquid state cultivation method is helpful to the production of monaclin K and monascin, his method still includes the main drawback of "lacking citrinin-inhibiting step".

So that, in view of the above-mentioned conventional red mold substrate preparation method (including the solid state cultivation method and the liquid state cultivation method) still have shortcomings and drawbacks, it is necessary to choose a fermented substrate with better effects and adjust the culture conditions to be optimum so as to increase the production of monaclin K, monascin and ankaflavin, and then to elevate the effects of blood-lipid lowering, blood-pressure lowering and atherosclerosis prevention. Therefore, the inventor of the present invention resorted to past experience, imagination, and creativity, performed experiments and researches repeatedly, and eventually devised the present invention: a method for manufacturing red mold dioscorea.

SUMMARY OF THE INVENTION

The first objective of the present invention is to provide a method for manufacturing red mold dioscorea, owing to the amounts of each kind of secondary metabolite produced by red mold yeast are variant under different cultural conditions, the manufacturing method and all the cultural conditions according to the present invention can promote the amount of formation of effective secondary metabolites, such as anti-inflammation material (monascin), anti-cancer material (ankaflavin) and cholesterol-lowering material (monacolin K), which can be used for compositions of drugs for lowering blood lipid, lowering blood pressure and preventing atherosclerosis.

Accordingly, in order to achieve the above-mentioned objectives of the present invention, the inventors propose a method for manufacturing red mold dioscorea, comprising the steps of:
(1) washing a fresh dioscorea clean and cutting the fresh dioscorea into pieces with a specific dimension, wherein the specific dimension is 2~20 mm;
(2) drying the pieces of the fresh dioscorea for making the dried dioscorea contain a specific water content and a specific sulfur content by a sulfuring method, wherein the specific water content is below 15%;
(3) adding a distilled water to the dried dioscorea for making the dried dioscorea and the water be a specific ratio in volume, wherein the specific ratio is 1:0.75 and this specific ratio make the dioscorea suitable to be executed a sterilization process;
(4) soaking the dried dioscorea in the distilled water for a specific time period;
(5) proceeding the sterilization process of the dioscorea at 121° C. for 20 min;
(6) spreading the steamed dioscorea in a wood dish for cooling the steamed dioscorea;
(7) inoculating the dioscorea with 5% *Monascus* spore solution;
(8) cultivating the inoculated dioscorea at a specific temperature and a specific cultural humidity for a specific cultural time period, wherein the specific cultural temperature is 30° C., the specific cultural humidity is 60%, and the specific cultural time period is 10 days;
(9) proceeding an anaerobic treatment to the product of the step (8) for a specific treating time period, wherein the anaerobic treatment is carried out by culturing the inoculated dioscorea under 100% $CO_2$ condition; and
(10) drying the product of the step (9) to a specific water content.

Moreover, for achieving the above-mentioned objectives of the present invention, the inventors propose a second embodiment of the method for manufacturing red mold dioscorea, comprising the steps of:
(1) adding a specific amount of water to a raw material of a dioscorea to make the raw material of the dioscorea and the water be a specific ratio, wherein raw material of the dioscorea is a dried dioscorea containing sulfur, and the sulfur contained by the dried dioscorea may contribute an acidic condition with pH 3-4, and the acidic condition being able to simulate the production of secondary metabolites of the red mold dioscorea when the red mold dioscorea is cultured;
(2) proceeding a sterilization process to the raw material of the dioscorea and then cooling the product down to a specific temperature;
(3) inoculating a *Monascus* spp. to the sterilized dioscorea;
(4) culturing the inoculated dioscorea under a specific cultural temperature and a specific shaking frequency for a specific cultural time period;
(5) proceeding an anaerobic treatment to the product of step (4) for a specific treating time period, wherein the anaerobic treatment is carried out by culturing the inoculated dioscorea under 100% $CO_2$ condition; and
(6) drying the product of step (5) to a specific water content, wherein the specific water content is below 15%.

DETAILED DESCRIPTION OF THE PREFERRED EMBODIMENTS

To achieve the foregoing objectives and effects, the inventors integrate red mold yeast with dioscorea and improve and amend the conditions of manufacturing methods, thus achieving the method for manufacturing red mold dioscorea of the present invention. Hereinafter, flowcharts of methods for manufacturing red mold dioscorea according to a first preferred embodiment and a second preferred embodiment of the present invention will be described in detail for illustrating the method for manufacturing red mold dioscorea.

Figure 1:
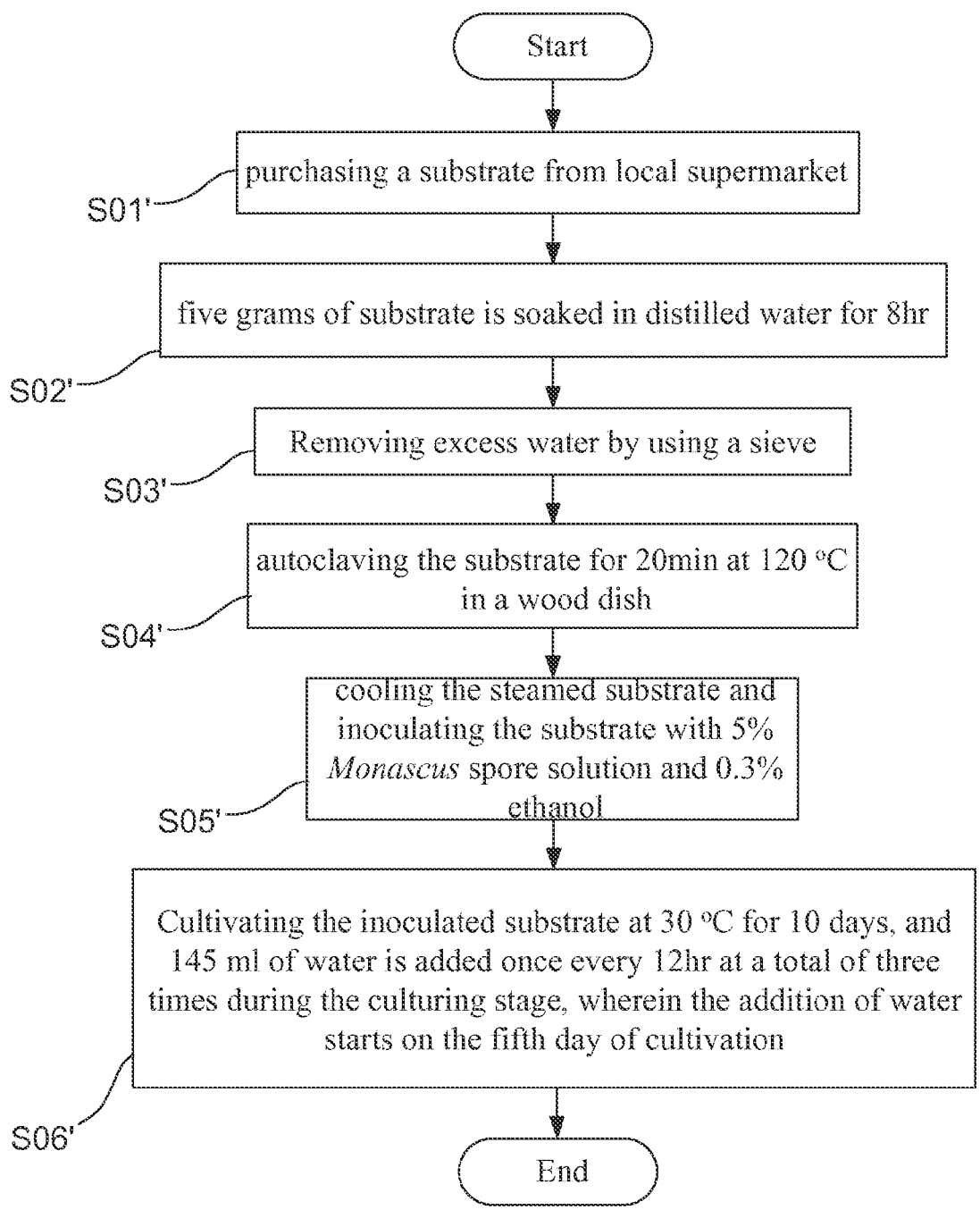
FIG. 1 is a flowchart of a red mold substrate preparation method proposed by Lee.
Figure 2:
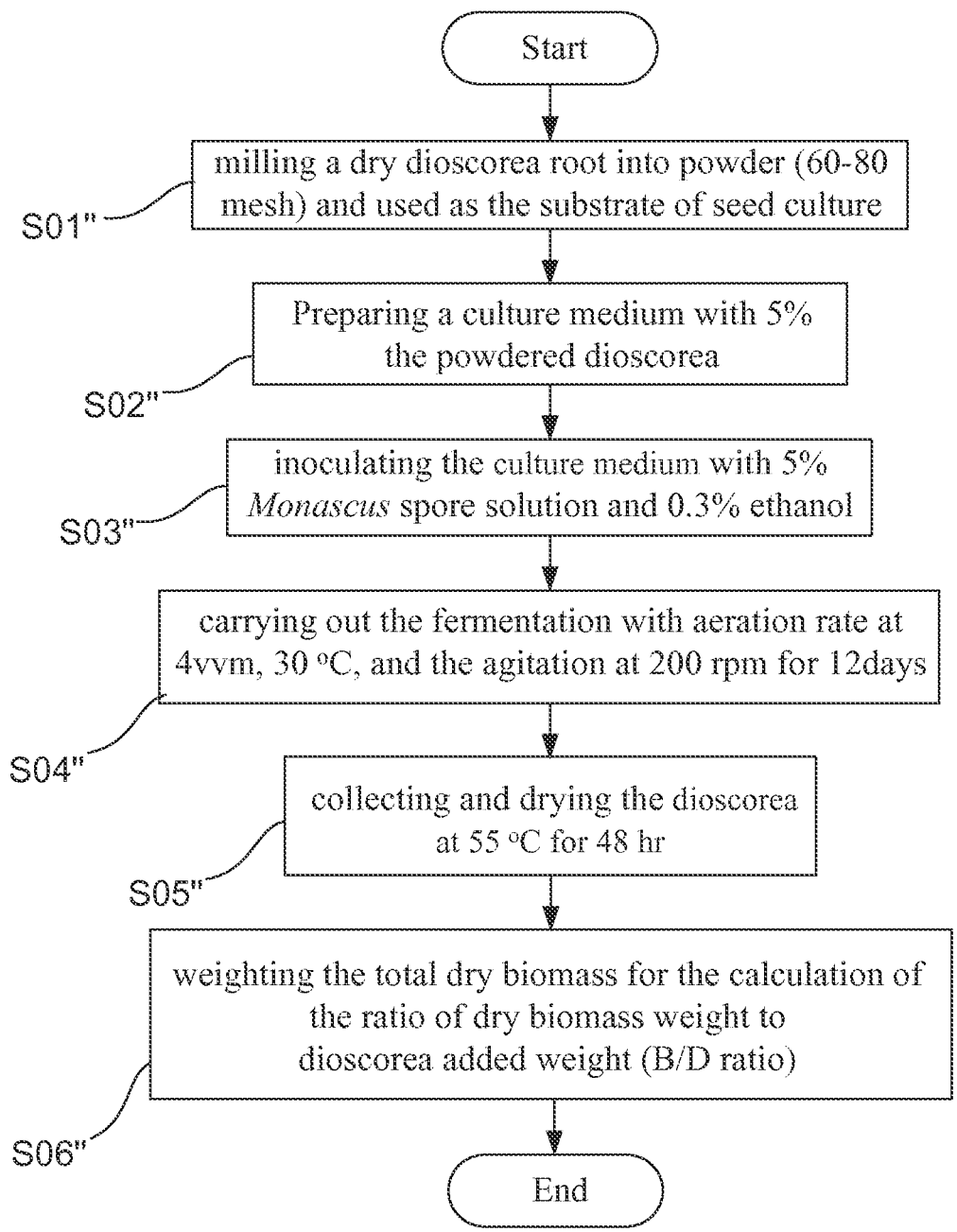
FIG. 2 is a flowchart of a liquid state cultivation method proposed by Lee.
Figure 3A:
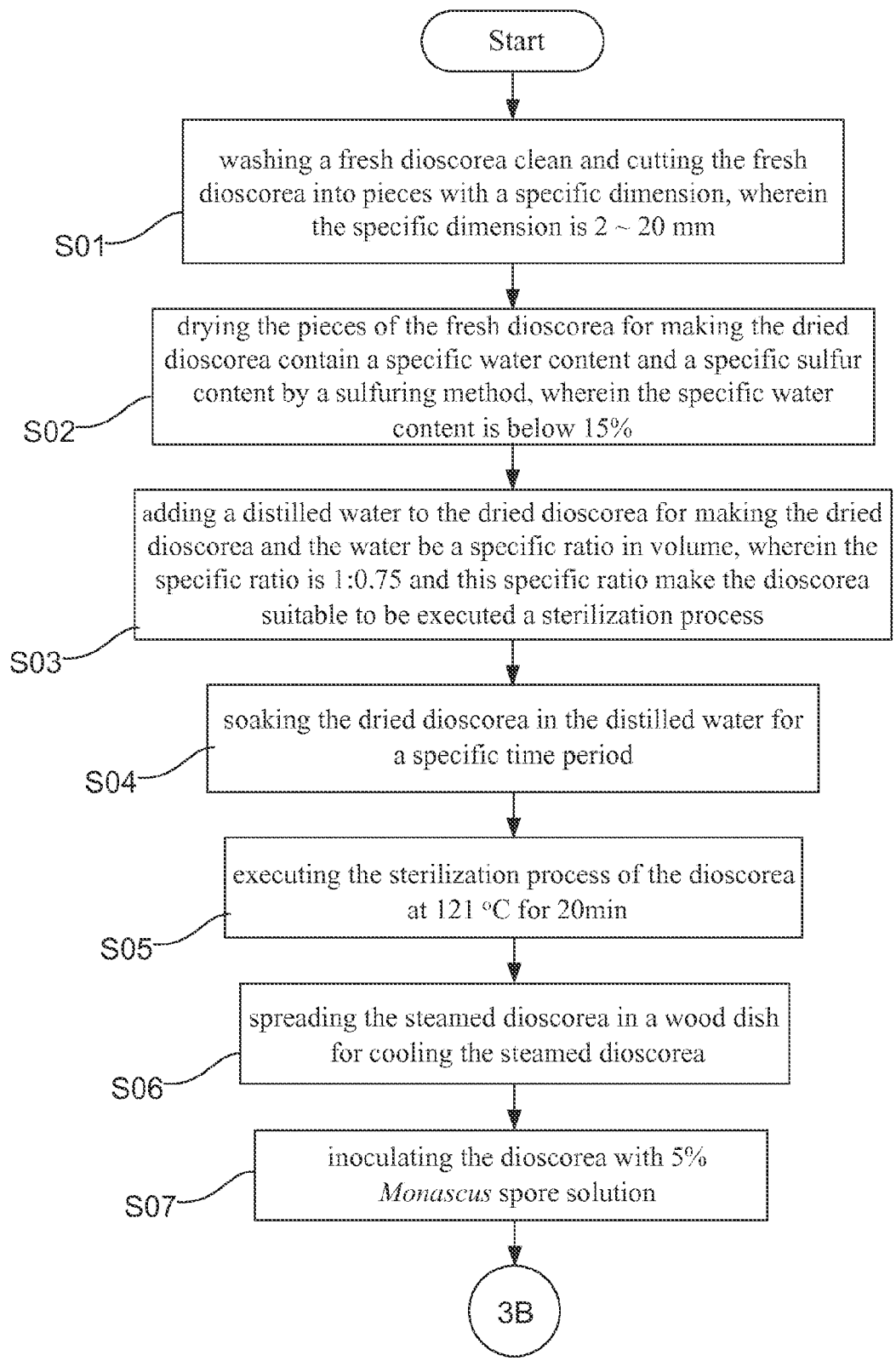
FIG. 3A and FIG. 3B are a flowchart of a method for manufacturing red mold dioscorea according to a first preferred embodiment of the present invention.
Figure 3B:
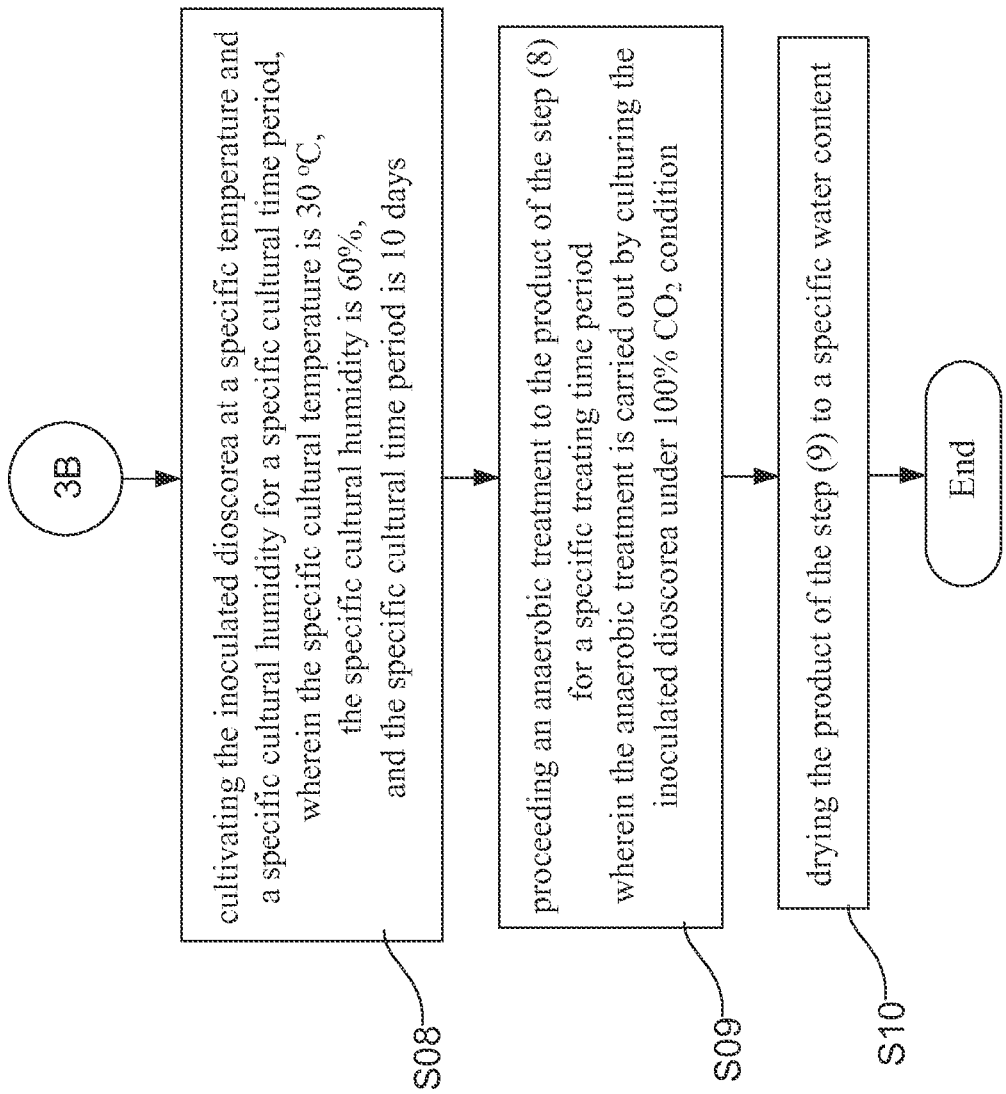

Referring to FIG. 3A and FIG. 3B, there are shown a flowchart of a method for manufacturing red mold dioscorea according to the first preferred embodiment of the present invention. As shown in FIGS. 3A and 3B, to execute the method for making a red mold dioscorea, it is firstly washing a fresh dioscorea clean and cutting the fresh dioscorea into pieces with a specific dimension (step S01), in which the specific dimension is 2~20 mm and the optimal dimension is 2 mm. The method is next to proceed step S02, drying the pieces of the fresh dioscorea for making the dried dioscorea contain a specific water content and a specific sulfur content by a sulfuring method, wherein the specific water content is below 15% and specific sulfur content is below 160 ppm. After step S02 is completed, step S03 is then proceeded for adding a distilled water to the dried dioscorea, so as to make the dried dioscorea and the water be a specific ratio in volume, wherein the specific ratio is 1:0.75 and this specific ratio make the dioscorea suitable to be executed a sterilization process.

Next, the method is proceeded steps S04 and S05 to soak the dried dioscorea in the distilled water for 60 minute and execute the sterilization process of the dioscorea at 121° C. for 20 min. And Step S06 is then executed in order to spread the steamed dioscorea in a wood dish for cooling the steamed dioscorea. So that, after the steamed dioscorea is cooled, the method next proceeds to step S07 for inoculating the dioscorea with 5% *Monascus* spore solution. The cultivate step, i.e., step S08, which is subsequently executed, such that the inoculated dioscorea is cultivated at a specific temperature and a specific cultural humidity for a specific cultural time period, wherein the specific cultural temperature is 30° C., the specific cultural humidity is 60%, and the specific cultural time period is 10 days.

Continuously, the method is proceeded steps S10 in order to proceed an anaerobic treatment to the product of the step S08 for a specific treating time period, wherein the anaerobic treatment is carried out by culturing the inoculated dioscorea under 100% $CO_2$ condition, and the specific treating time period is 48 hr. Eventually, step S10 is executed for drying the product of the step S09 to a specific water content, wherein the specific water content is below 15%.

In recent years, the secondary metabolites of red mold yeast are paid more and more attention by people, wherein monascin and ankaflavin, the yellow pigments, are proved to be the anti-inflammation agents and the active ingredients for lowering the incidence of cancer, and monacolin K is an effective cholesterol-lowering material, thus promoting the contents of monascin, ankaflavin and monacolin K in the *Monascus* fermented products is recently an important goal for *Monascus* researches.

In the past, red mold related products are all made from rice as the fermented substrate, but the yields of anti-inflammation material (monascin), anti-cancer material (ankaflavin) and cholesterol-lowering material (monacolin K) are not abundant in red mold rice. In order to increase the amounts of these active ingredients, Lee et al. propose a solid state cultivation method for increasing the production of monaclin K and monascin. However, Lee's method includes the shortcomings and drawbacks of (1) failing to optimize a best water ratio for soaking the substrate; (2) does not provide a suitable environment for culturing the inoculated substrate; and (3) adding 0.3% (v/w) ethanol to substrate (dioscorea) in order to lower the production of citrinin, one kind of polyketide derivatives of *Monascus*.

The aforesaid first preferred embodiment of the method introduced by the present invention is also a solid state cultivation method for increasing the production of the secondary metabolites of red mold, such as monacolin K, monascin and ankaflavin. In the method of the present invention, dioscorea is soaked in a distilled water with the dried dioscorea and the water having a specific ratio (1:0.75) in volume, and this optimal ratio is suitable to the sterilization process of the dioscorea. Moreover, when the inoculated dioscorea is cultivated, the sulfurized dioscorea fabricated by the step S02 is able to stimulate the production of monascin and ankaflavin by 1.5 and 1.3 times via an acidic condition (pH 3-4) contributed from $S_2$. In addition, in the method of the present invention, the 60% of controlled environment humanity is useful to stabilize the production of monacolin K, monascin and ankaflavin, and such environment humanity control is easier to be applied on a large industrial scale than water supplementation.

Furthermore, in order to effectively inhibit the production of citrinin but keep the production of monacolin K, monascin and ankaflavin, an anaerobic treatment is adopted in the method of the present invention and carried out by culturing the inoculated dioscorea under 100% $CO_2$ condition. In the solid fermentation of the present invention, anaerobe treatment can obviously decrease the citrinin concentration by 2.1 times. Therefore, according to above descriptions of the first preferred embodiment of the method for manufacturing red mold dioscorea, it believes that the red mold dioscorea can be manufactured successfully by utilizing the method of the present invention.

Figure 4:
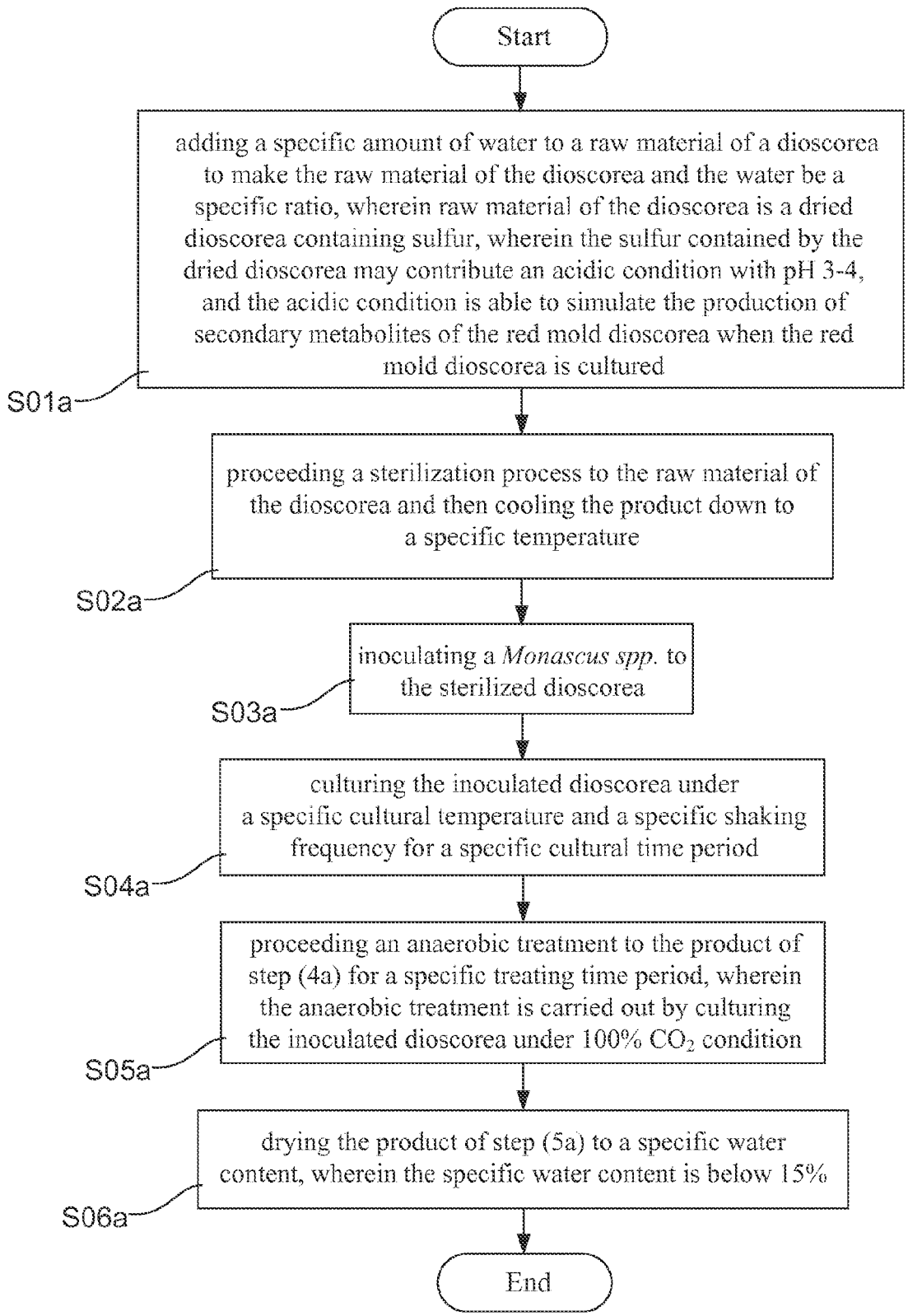
FIG. 4 is a flowchart of the method for manufacturing the red mold dioscorea according to a second preferred embodiment of the present invention.

Please refer to FIG. 4, which illustrates a flowchart of a method for manufacturing red mold dioscorea according to the second preferred embodiment of the present invention. The method for manufacturing red mold dioscorea of the present invention not only includes the first preferred embodiment but also has a second preferred embodiment; the second preferred embodiment is a liquid state cultivation method. As shown in FIG. 4, to execute the second preferred embodiment, it is firstly adding a specific amount of water to a raw material of a dioscorea to make the raw material of the dioscorea and the water be a specific ratio (step S01a), wherein the specific ratio is ranged from 1:10 to 1:200, and the raw material of the dioscorea is a dried dioscorea with sulfur below 15%, so as to keep the sulfur content is below 160 ppm. In the method of second preferred embodiment, the sulfur contained by the dried dioscorea may contribute an acidic condition with pH 3-4, and the acidic condition is able to simulate the production of secondary metabolites of the red mold dioscorea when the red mold dioscorea is cultured.

Next, the method proceeds to step S02a for proceeding a sterilization process to the raw material of the dioscorea at 121° C. for 30 minutes, and then cooling the product down to a specific temperature. After the dioscorea is cooled, step S03a is subsequently executed for inoculating a *Monascus* spp. to the sterilized dioscorea. Then, in step S04a, it cultures the inoculated dioscorea under a specific cultural temperature and a specific shaking frequency for a specific cultural time period, wherein the specific cultural temperature in the step S04a is 25~37° C., the specific shaking frequency is 50~300 rpm, and the specific cultural time period is 8~20 days. During the culture, in order to inhibit the production of citrinin, it needs to proceeding an anaerobic treatment to the cultured dioscorea for 48 hr, and n the anaerobic treatment is carried out by culturing the inoculated dioscorea under 100% $CO_2$ condition. Therefore, after the anaerobic treatment is finished, the step S06a is then executed for drying the *Monascus*-fermented dioscorea with the water content, below 15%.

Therefore, Comparing to the conventional liquid state cultivation method proposed by Lee et al., the introduced liquid state cultivation method according to the second preferred embodiment of the present invention includes the main advantage as following: citrinin-inhibiting step is adopted in the liquid state cultivation method of the present invention, the citrinin-inhibiting step is carried out by culturing the inoculated dioscorea under 100% $CO_2$ condition. Moreover, it needs to especially note that this citrinin-inhibiting step (i.e., anaerobic treatment) would not simultaneously decease the production of the secondary metabolites of the *Monascus*-fermented dioscorea.

According to above descriptions, it believes that red mold dioscorea (i.e., *Monascus*-fermented dioscorea) can be manufactured successfully according to the method of the present invention. There are large differences in the appearances between red mold dioscorea and red mold rice, wherein the largest distinction is that the major pigment produced by red mold rice is red pigment and the appearance of red mol dioscorea is orange-yellow.

Figure 5:
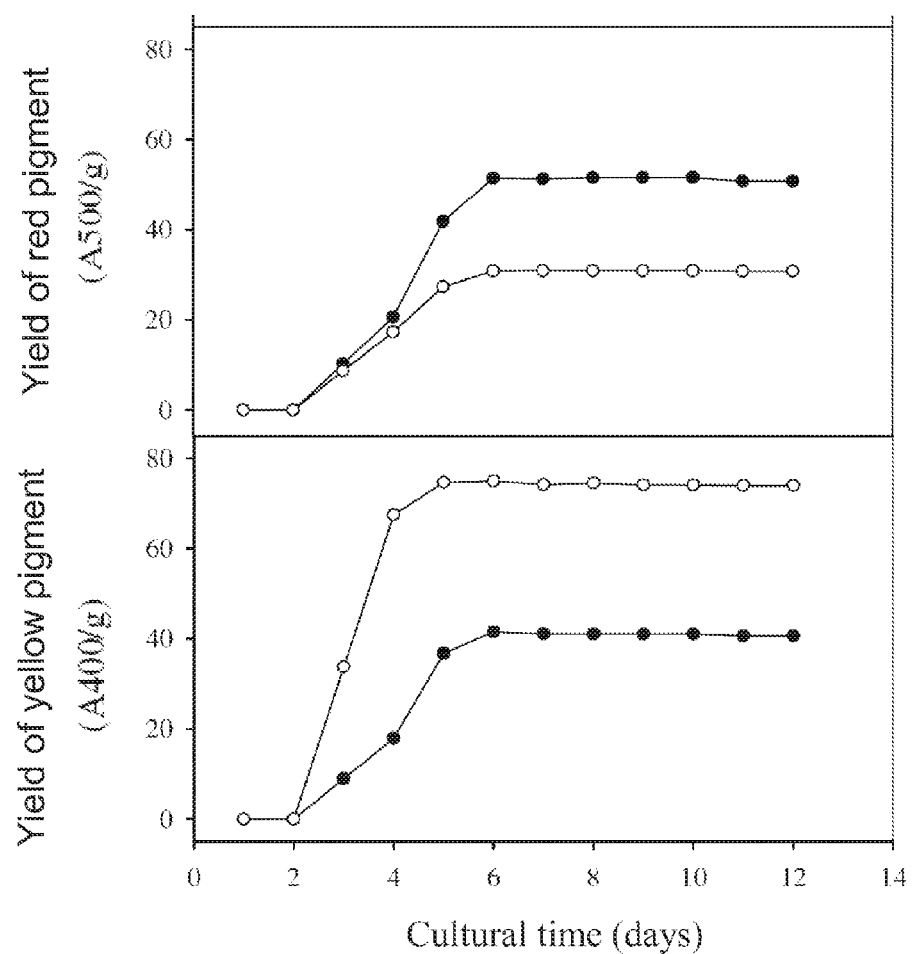
FIG. 5 is a trend graph of yellow pigment and red pigment formation in the cultural processes of the red mold rice and red mold dioscorea.

Referring to FIG. 5, which is a trend graph of yellow pigment and red pigment formation in the cultural processes of red mold rice (solid circle) and red mold dioscorea (hollow circle). A large amount of yellow pigment is produced by red mold dioscorea in the initial stage, and the yield of yellow pigment in red mold dioscorea is higher than that in red mold rice; in terms of red pigment, the yield of red pigment in red mold dioscorea is lower than that in red mold rice. These results demonstrate that red mold yeast fermented with dioscorea can produce a large amount of yellow pigment containing some active ingredients, such as monascin and ankaflavin.

Referring to the following table 1, which compares the yield of monascin, ankaflavin and GABA in red mold dioscorea and red mold rice cultured with different methods.

TABLE 1

| | Monascin (mg/kg) | Ankaflavin (mg/kg) | GABA (mg/kg) |
|---|---|---|---|
| Red mold rice - solid state cultivation | 3547 | 1598 | 131 |
| Red mold dioscorea - solid state cultivation | 15011 | 10074 | 513 |
| Red mold rice - liquid state cultivation | 5415 | 2488 | 45 |
| Red mold dioscorea - liquid state cultivation | 23280 | 15330 | 46 |

As shown in the table 1, the yield of monascin in red mold dioscorea resulted from solid state cultivation is 4.23 times more than that in red mold rice resulted from solid state cultivation, and the yield of ankaflavin in red mold dioscorea resulted from solid state cultivation is elevated by 6.30 times significantly contrasting with red mold rice. This shows that the contents of monascin and ankaflavin in red mold dioscorea cultured by solid state cultivation is higher than that in red mold rice cultured by solid state cultivation. Red mold dioscorea produced by liquid state cultivation has the same effects as above results. The contents of monascin and ankaflavin in red mold dioscorea cultured by liquid state cultivation are 4.30 and 5.16 times respectively more than that in red mold rice cultured by liquid state cultivation. Furthermore, the production quantity of GABA is also higher in the cultural products in red mold dioscorea.

Figure 6:
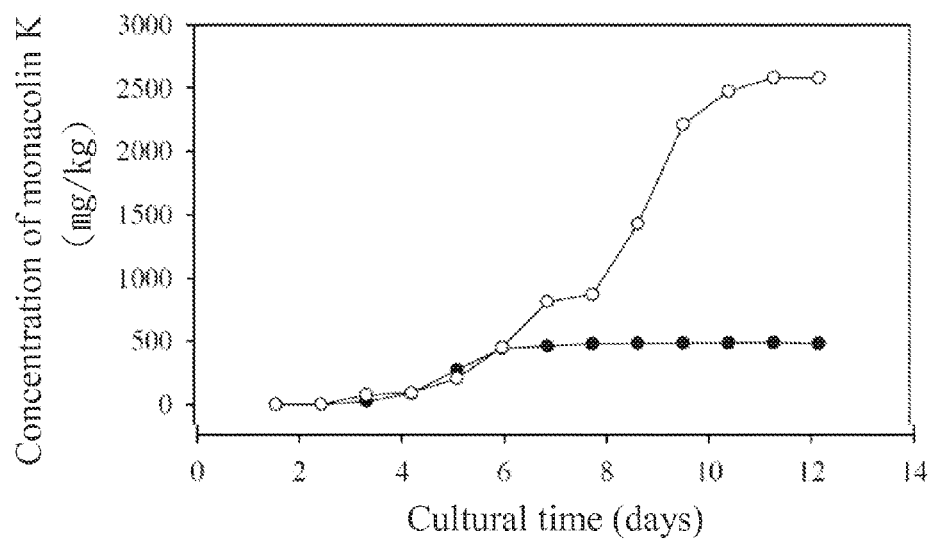
FIG. 6 is a trend graph of monacolin K formation in the cultural processes of the red mold rice and red mold dioscorea.

Referring to FIG. 6, which is a trend graph of monacolin K formation in the cultural processes of red mold rice (solid circle) and red mold dioscorea (hollow circle). The trend graph illustrates that the slow production of monacolin K in red mold rice begins at the second day of the cultivation and stagnates at the sixth day; red mold dioscorea produces monacolin K constantly until the tenth day, wherein the production of monacolin K is very rapid from the fifth day to the tenth day. Additionally, after completing the cultivation, the yield of monacolin K in red mold dioscorea is over 5 times more than that in red mold rice.

Referring to the following table 2, which compares that the yields of monacolin K, red pigment and yellow pigment in several kinds of substrates.

TABLE 2

| | Monacolin K (mg/kg) | Red pigment (A500/g) | Yellow pigment (A400/g) |
|---|---|---|---|
| dioscorea | 2584 ± 127 | 30 ± 5.0 | 74 ± 4.7 |
| rice | 481 ± 33 | 50 ± 4.2 | 41 ± 4.8 |
| cassava | 522 ± 34 | 50 ± 3.8 | 34 ± 3.8 |
| Sweet potato | 196 ± 21 | 51 ± 3.2 | 39 ± 3.9 |
| potato | 495 ± 37 | 48 ± 6.9 | 32 ± 4.8 |

As shown in the table 2, it is obvious that the yield of monacolin K in red mold dioscorea is 5.27 times more than that in red mold rice, 4.95 times more than that in cassava, 13.18 times more than that in sweet potato, and 5.22 times more than that in potato. Thus, dioscorea is the best substrate for producing monacolin K in these substrates. Furthermore, the table 2 also indicates that the yield of yellow pigment in red mold dioscorea is higher than that in other substrates, hence red mold dioscorea indeed can promote the yield of yellow pigment, such as monascin and ankaflavin.

From the above researches, the results demonstrate that red mold dioscorea possesses higher yields of monascin, ankaflavin, GABA, and monacolin K, which are active ingredients with the effects of anti-inflammation, anti-cancer, blood pressure lowering, nerve conduction promoting, and cholesterol lowering, and can achieve well effects of blood lipid lowering, blood pressure lowering, atherosclerosis preventing, and Alzheimer's disease improving, thus red mold dioscorea is highly important in the researches and developments of health foods in future. The present invention opens up and develops red mold dioscorea possessing higher yields of functional metabolites comparing with that in red mold rice, and it is expected to be contributive to the developments of *Monascus* related products.

The foregoing embodiments are provided to illustrate and disclose the technical principles and features of the present invention so as to enable persons skilled in the art to understand the disclosure of the present invention and implement the present invention accordingly, and are not intended to be restrictive of the scope of the present invention. Hence, all equivalent modifications and variations made to the foregoing embodiments without departing from the spirit and principles in the disclosure of the present invention should fall within the scope of the invention as set forth in the appended claims.

What is claimed is:

1. A method for manufacturing red mold dioscorea comprising the steps of:
   (1a) adding a specific amount of water to a raw material of a dioscorea to make the raw material of the dioscorea and the water be a specific ratio ranged from 1:10 to 1:200, wherein the raw material of the dioscorea is a dried dioscorea containing a sulfur content is below 160 ppm;
   (2a) proceeding a sterilization process to the raw material of the dioscorea and then cooling the product down to a specific temperature;
   (3a) inoculating a *Monascus* spp. to the sterilized dioscorea;
   (4a) culturing the inoculated dioscorea under a specific cultural temperature ranged from 25° C. to 37° C. and a specific shaking frequency ranged from 50 rpm to 300 rpm for 8~20 days; wherein the $S_2$ included by the specific sulfur content below 160 ppm would contribute an acidic culturing condition with pH 3-4, and the acidic culturing condition being able to increase the production of a yellow pigment of secondary metabolites produced by the *Monascus*-inoculated dioscorea;

(5a) proceeding an anaerobic treatment to the product of step (4a) for 48 hours, wherein the anaerobic treatment is carried out by culturing the inoculated dioscorea under 100% $CO_2$ condition; and (6a) drying the product of step (5a) to a specific water content, wherein the specific water content is below 15%.

2. The method for manufacturing red mold dioscorea according to claim 1, wherein the sterilization process in the step (2a) is carried out at 121° C. for 30 minutes.

3. The method for manufacturing red mold dioscorea according to claim 1, wherein the product of the step (5a) can be treated with a centrifugation process before going to step (6a).

4. The method for manufacturing red mold dioscorea according to claim 1, wherein the yellow pigment at least includes a monascin and an ankaflavin.

* * * * *